US006376441B1

(12) United States Patent
Ross et al.

(10) Patent No.: US 6,376,441 B1
(45) Date of Patent: Apr. 23, 2002

(54) MULTI-PHASE MELT CAST TOILET BAR AND A METHOD FOR ITS MANUFACTURE

(75) Inventors: Michael Edward Ross, Oxford; Thomas Daniel Arkins, Ridgefield; Robert Alfread Bennett, Easton; Syed Husain Abbas, Seymour, all of CT (US)

(73) Assignee: Unilever Home and Personal Care USA, division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/605,063

(22) Filed: Jun. 28, 2000

Related U.S. Application Data

(60) Provisional application No. 60/149,410, filed on Aug. 17, 1999.

(51) Int. Cl.[7] .................................................. A61K 7/50

(52) U.S. Cl. ......................... 510/146; 510/151; 510/153

(58) Field of Search ................................. 510/130, 141, 510/151, 153, 146

(56) References Cited

U.S. PATENT DOCUMENTS

| | | |
|---|---|---|
| 4,996,000 A | 2/1991 | Redeker |
| 5,198,140 A | 3/1993 | Joshi et al. |
| 5,217,639 A | 6/1993 | Mottola |

FOREIGN PATENT DOCUMENTS

| | | |
|---|---|---|
| EP | 0 366 209 | 5/1990 |
| EP | 41 07 445 A1 | 9/1992 |
| JP | 59-157200 | 9/1984 |
| WO | 00/09078 | 2/2000 |

OTHER PUBLICATIONS

International Search Report PCT/EP 00/07144 dated Jan. 19, 2001 (4 pages).

*Primary Examiner*—Necholus Ogden
(74) *Attorney, Agent, or Firm*—Alan A. Bornstein

(57) ABSTRACT

A multi-phase melt cast toilet bar which has at least one interface along a plane perpendicular to the plane formed by the x and y-axis of said bar, and a process of making the bar is described. Each phase, containing a cleansing agent, is reproducibly positioned in the bar to be used simultaneously thereby allowing the user to simultaneously derive benefits from the use of the cleansing agents contained in the bar's layers. The process for making the bar is a continuous one, whereby the molten cleansing agents are simultaneously or separately poured into the mold, simultaneously or separately allowed to harden, and where the mold divider is not removed or removed either after hardening of the adjacent molten cleansing agent but before the pouring of the next molten cleansing agent, or removed while at least one phase remains flowable. The hardened multi-phase toilet bar is finally ejected from the mold.

20 Claims, 4 Drawing Sheets

MULTI-PHASE MELT CAST TOILET BAR AND A METHOD FOR ITS MANUFACTURE

PRIORITY

This application claims priority to provisional application No. 60/149,410 filed Aug. 17, 1999.

BACKGROUND OF THE INVENTION

This invention relates generally to cleansing bars, and more particularly to cleansing bars having a plurality of layers of different materials oriented along a plane perpendicular to the plane formed by the x and y-axis of said bar.

DESCRIPTION OF THE RELATED ART

Solid cleansing materials in the form of bars or cakes have been commercially available for many years. These bars may consist of soaps or detergents and may contain various other substances such as colouring materials, perfumes, benefiting agents, moisturisers and fillers. Different cleansing bar formulations are used to accomplish different cleansing needs. For example, skin on some parts of the body may be more sensitive than other areas. Some body areas are also more prone to perspire than other areas. In addition, the hands are more often exposed to more hard to remove dirt and grease than the rest of the body. These divergent cleansing problems have lead to the production of different cleansing bars designed for such different needs. Moreover, various individuals in the household may have different preferences or needs so that the household may keep on hand, at the lavatory or the shower, several different cleansing bars.

European Patent Application No. 366209 titled "Method of Production of Tablets of Toilet", published May 2, 1990, and U.S. Pat. No. 4,996,000 titled "Multi-Layer Cleansing Bar", issued to Dale R. Redeker on Feb. 26, 1999 both disclose a cast moulded cleansing bar having a plurality of layers of different cleansing materials oriented along a plane parallel to the plane formed by the x and y-axis.

As used herein, the x axis is positioned along the longest dimension of the bar, typically the length, the y axis is positioned along the $2^{nd}$ longest dimension, typically the width, and the z axis is positioned along the shortest dimension of the bar, typically the height.

Bars having layers oriented along a plane parallel to the plane formed by the x and y-axis of the bar are characterised in that the user must rotate the bar in order to contact a substantial area of a different cleansing material. These bars are usually made using a layer by layer cast molding or an extrusion process. On the other hand, the user would not have to rotate the toilet bar in order to simultaneously contact substantial areas of different cleansing materials using the inventive toilet bar.

U.S. Pat. No. 5,198,140 titled "Dual Composition Toilet or Detergent Bar Containing Convoluted Surfaces and Tongue and Groove Interlock" issued to David Joshi et al., on Mar. 30, 1993, discloses an extrusion formed dual composition bar, the two layers of which are oriented along a plane parallel to the plane formed by the x and y-axis of the bar of the bar. Japanese Patent Kokai Application No. 59-157200, published in Sep. 6, 1984, discloses a two phase toilet bar where the boundary layer is oriented along the bar's plane perpendicular to the plane formed by the x and y-axis of the bar. This two phase is made by melting casting a first cleansing composition, removing the first casting from the mold, spraying with coloring pigment, cutting the casting to shape a decorative curve, repositioning the cut first casting in a mold, and casting a second cleansing composition, which adheres to the first cleansing composition layer, to form a two phase bar with a curvilinear boundary layer. Although the finished bar of JP 59-157200 may be produced in a reproducible fashion, this process is disadvantageous because of the many separate manufacturing steps required. U.S. Pat. No. 5,217,639 titled "Dual Phase Toilet Bar Containing a Clear Portion and an Opaque Portion Joined Along a Single Curvilinear Shaped Surface" issued to Nicolas Mottola on Jun. 8, 1993, discloses a dual phase toilet bar where the interface layer between the two phases of the bar is located generally along the plane parallel to the plane formed by the x and y-axis. The bar is cast by a sequential molding technique wherein a first molten toilet composition is poured into a plastic mold filing the mold to the 50% mark, allowed to harden, and then a second molten toilet composition is poured into the mold and subsequently allowed to harden. One disadvantage of this molding technique is the variability of the boundary line that is obtained between the two cleansing materials.

None of the foregoing patents however, disclose a toilet bar with multi-layers cast along a straight or curvilinear plane perpendicular to the plane formed by the x and y-axis of said bar, nor a molding process where a formed divider is used to control the shape of each layer reproducibly in a multi-layer toilet bar such that the shape of the boundary layer can be custom made and is consistent from bar to bar. A distinct drawback of bars that are cast without formed dividers is that they may display random variation with the position of the boundary between the different cleansing compositions.

SUMMARY OF THE INVENTION

In one aspect, the present invention relates to a multi-layer toilet bar containing a plurality of layers of cleansing material which are oriented to give maximum simultaneous benefit to the user of the toilet bar. In another aspect of the present invention, multi-layer toilet bars are provided with highly reproducible boundary lines between each layer. In another aspect of the present invention, a multi-layer toilet bar is provided that functions similarly to conventional toilet bar and its cleansing activity yet can provide skin benefits associated with different cleansing material compositions. A further aspect of the present invention is to provide a multi-layer toilet bar wherein certain active ingredients are incorporated into one layer but, not in the other. A still further aspect of the present invention is to provide a process for manufacturing a multi-layer toilet bar wherein a highly reproducible plurality of boundary layers oriented along the plane perpendicular to the plane formed by the x and y-axis of the bar is obtainable. These and other aspects of the present invention will become more apparent from the summary, detailed description, and examples which follow.

A multi-layer toilet bar is provided comprising a plurality of layers of cleansing materials, the layers having a common interface along said bar's flat or curvilinear plane perpendicular to the plane formed by the x and y-axis of said bar and said layers having been melt cast in a unitary mold having a cavity and at least one removable formed divider contained within said cavity. The multi-layer bar is cast using a melt casting process that is continuous whereby the casting is not removed from the mold prior to completion of casting the finished toilet bar. Preferably, the multi-layer toilet bar has two layers of cleansing material and the mold has one removable formed divider. The formed divider can be slidably positioned in the mold cavity and in another aspect can be pivotally positioned in the mold cavity in a first position and the like. Preferably, the formed divider has a curvilinear shape.

Preferably one of the layers of the multi-layer toilet bar is composed of a cleansing material which lathers and another layer is composed of a cleansing material which moisturises the skin. A first melt casting process for making the multi-layer toilet bar is also provided which comprises the steps of: positioning at least one removable formed divider along a flat or curvilinear plane perpendicular to the plane formed by the x and y-axis of said bar in a unitary mold cavity to form at least two cavities; pouring a molten cleansing material into a first cavity defined by said mold and the removable divider; cooling the molten cleansing material until it is hardened sufficiently so that the formed divider can be removed from the mold; removing the divider from the mold either by sliding, pivoting or the like; pouring a second molten cleansing material into the mold cavity defined by the first hardened material and the mold; cooling the second molten cleansing material until it is hardened, and finally ejecting a hardened multi-layer toilet bar casting from the mold. Preferably, the process is continuous wherein the melt casting is not removed from the mold prior to completion of the casting of the finished bar. In another embodiment, a plurality of molten cleansing materials at a first temperature can be poured simultaneously or consecutively into their respective cavities, the molten material allowed to cool to a semi-solid state at a second temperature, and the removable dividers are then removed from the mold while at least one of the molten cleansing materials at said second temperature is hot enough to both flow away from the removable divider and fill the space in the mold formerly occupied by the divider. Preferably two molten materials are poured into two separate cavities divided by a single removable divider. In the case of the simultaneous pouring of a plurality of molten materials, the removable divider is preferably removed before the molten material cools to a second temperature of 85° C. Preferably, only one removable divider is positioned in the mold cavity and made to be slidably removed from the mold or pivotally removed from the mold. Preferably the multi-cleansing material is cooled by a method selected from the group consisting of refrigeration, cryogenics, ambient air cooling, and the like. In another embodiment of the inventive bar and process, at least one of the removable formed dividers may be a water soluble or water dispersible solid material, preferably a solid cleansing material, which is not removed after casting the adjacent layers whereby the divider becomes part of the finished bar.

DETAILED DESCRIPTION OF THE INVENTION

Figure 1:
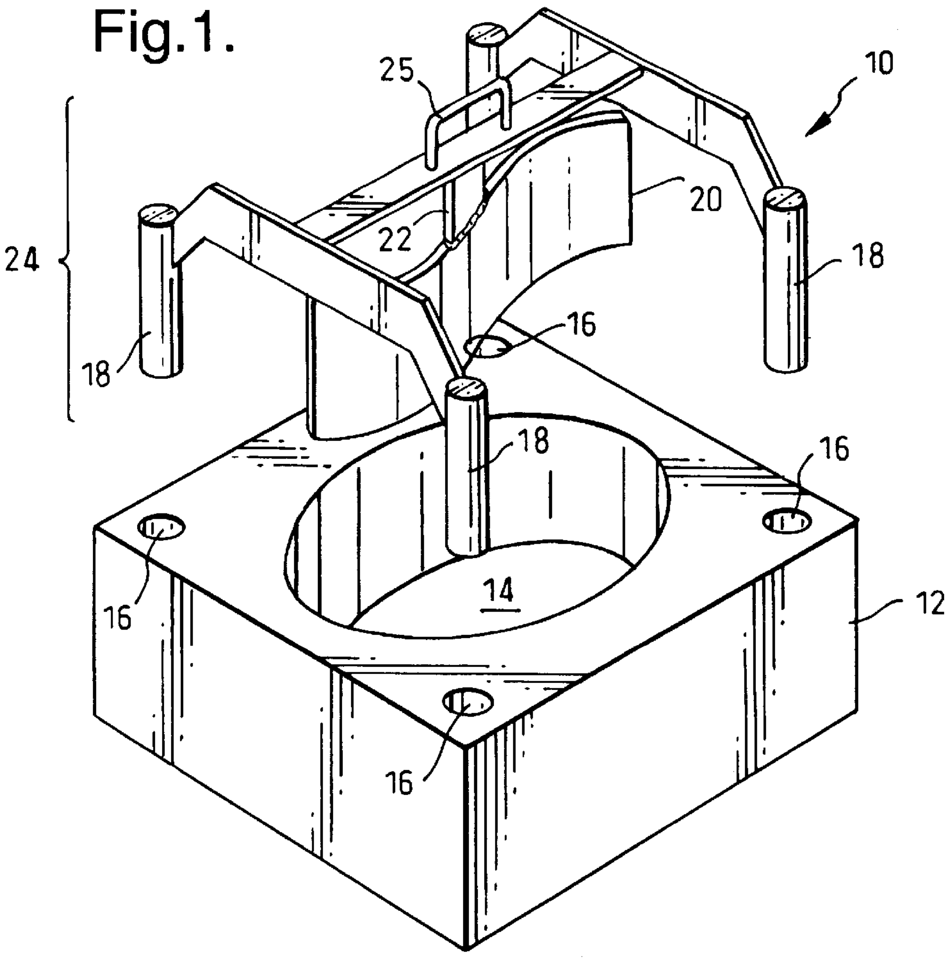
FIG. 1. Is a perspective diagrammatic view of a formed divider being received in one embodiment of a unitary mold of the present invention.

Referring to FIG. 1, casting assembly 10 includes unitary bottom mold 12, having a mold cavity 14 and locating apertures16. Also depicted in FIG. 1, is divider assembly 24 being received into unitary bottom mold 12. Divider assembly 24 includes former divider 20, which is attached to divider assembly 24 via clip 22. Divider assembly 24 also includes handle 25 and locating pins 18. Locating pins 18 are received into their respective locating apertures 16 when the formed divider 20 is properly positioned in unitary bottom mold 12 and mold cavity 14.

Figure 2:
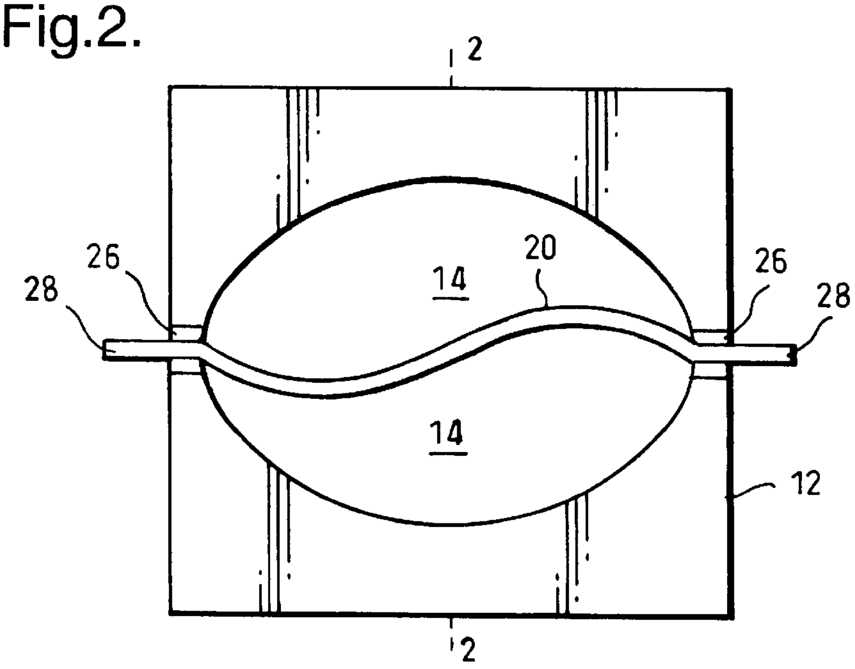
FIG. 2. Is a top planar view of a second embodiment of a unitary mold of the present invention.

FIG. 2 illustrates a top planar view of a second embodiment of casting assembly 30. Casting assembly 30 includes unitary bottom mold 12, formed divider 20, and mold cavity 14. In position 1, formed divider 20, is a slidably positioned in casting assembly 30 when divider handles 28 are positioned in locating aperture 26. In position 2, formed divider 20 is slidably removed from casting assembly 30. Divider handles 28 are rigidly affixed to formed divider 20.

Figure 3:
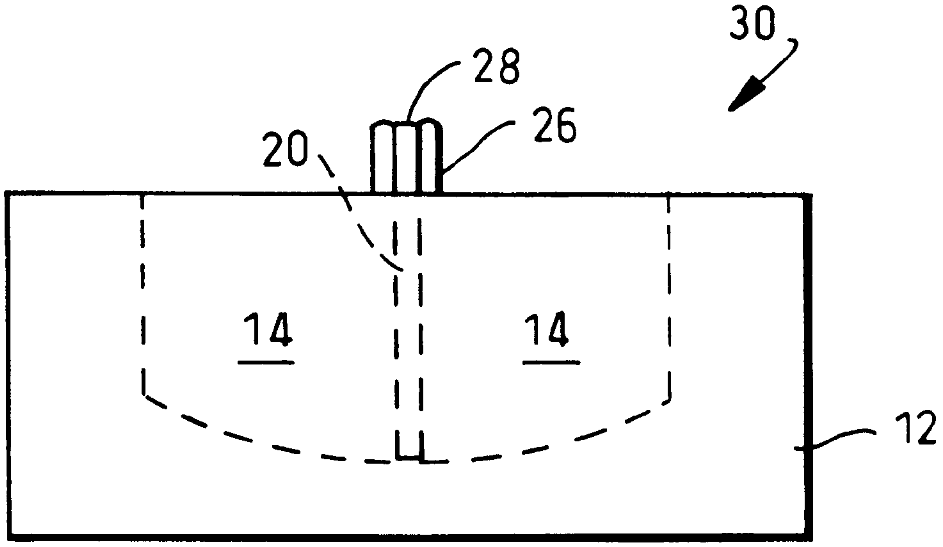
FIG. 3. Is a cross section taken along line 2—2 of FIG. 2.
Figure 4:
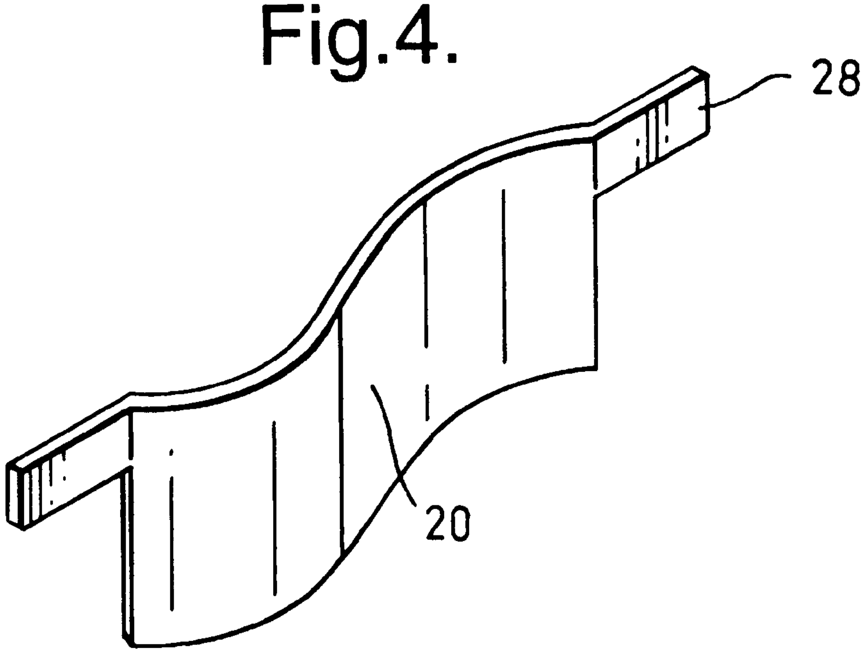
FIG. 4. Is a perspective view of the formed divider illustrated in FIG. 2.

FIG. 3 showing a cross section taking along line 2—2 of FIG. 2. FIG. 4 shows a perspective view of the formed divider 20 of FIG. 2 that has been slidably removed from casting assembly 30 in position 2.

Figure 5:
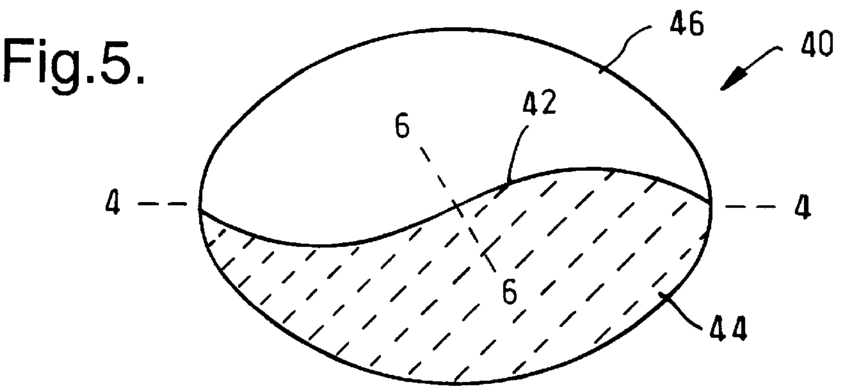
FIG. 5. Is a top planar view of one embodiment of a toilet bar of the present invention.
Figure 6:
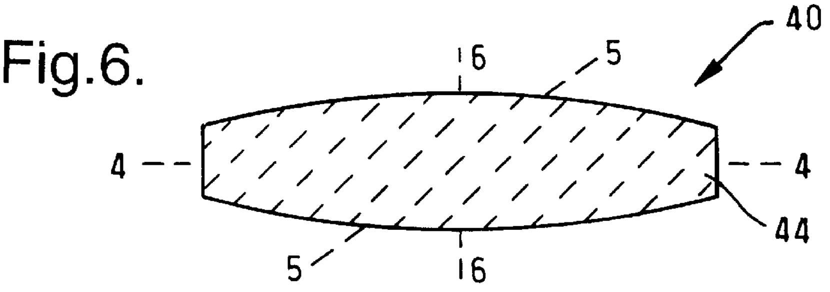
FIG. 6. Is a cross section taken along line 4—4 of FIG. 5.
Figure 9:
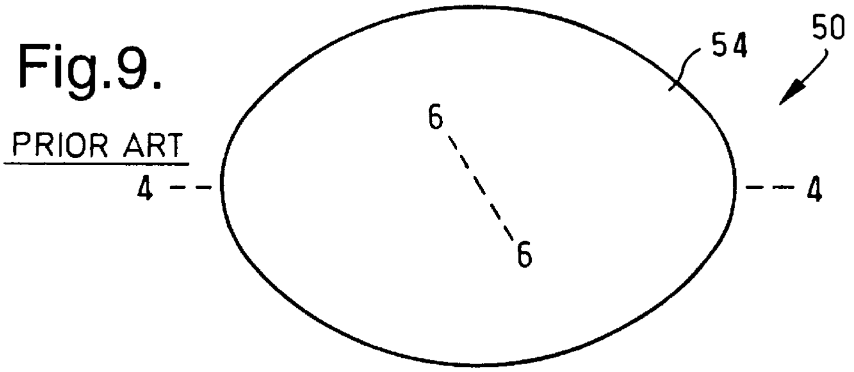
Fig.9. PRIOR ART
FIG. 9. Is a top planar view of a prior art toilet bar.
Figure 10:
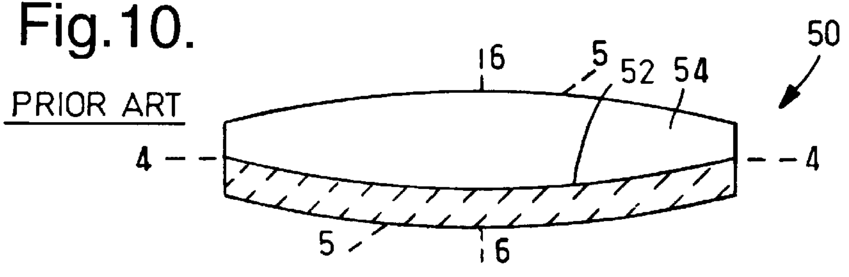
Fig.10. PRIOR ART
FIG. 10. Is a cross section taken along line 4—4 of FIG. 9.
Figure 7:
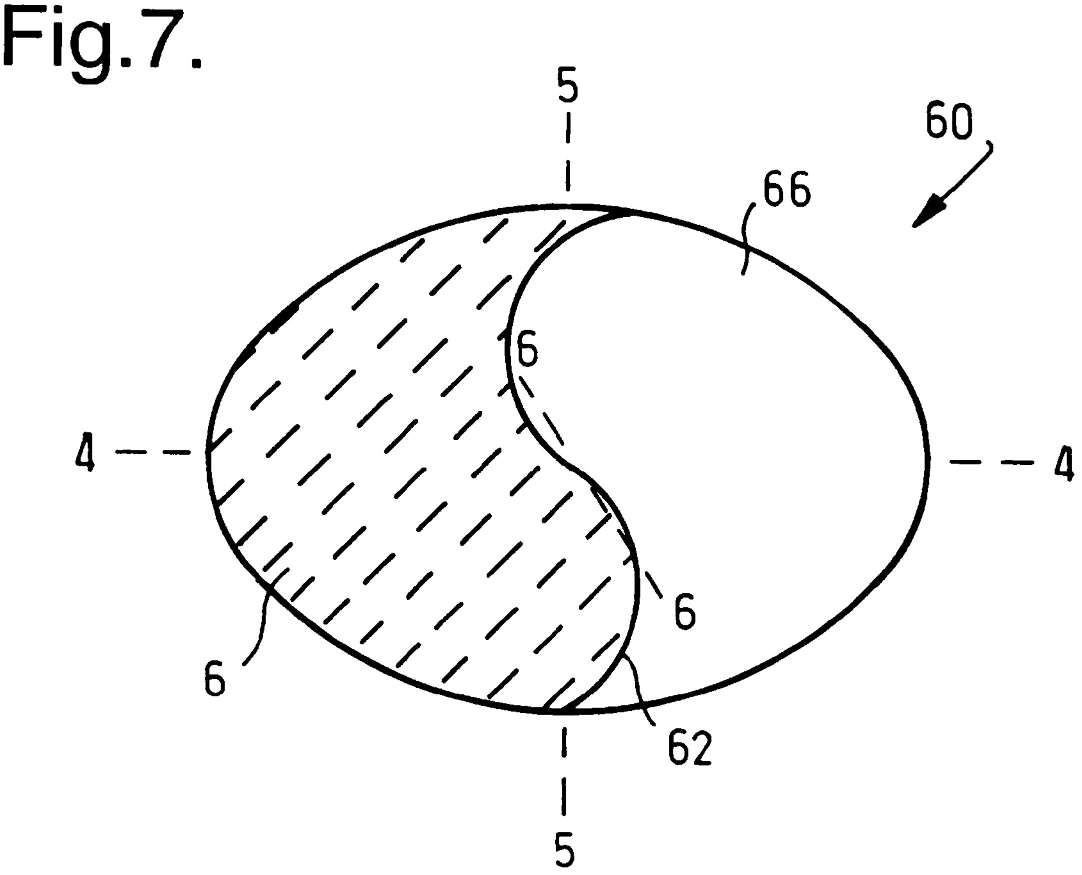
FIG. 7. Is a top planar view of another embodiment of a toilet bar of the present invention.
Figure 8:
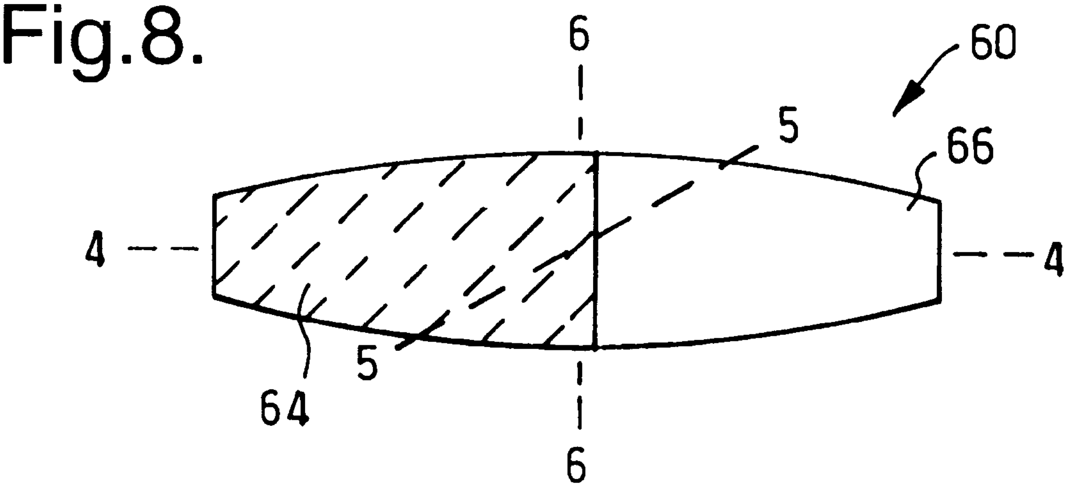
FIG. 8. Is a cross section taken along line 4—4 of FIG. 7.

FIG. 5 is a top planar view of one embodiment of a toilet bar 40 of the present invention. Toilet bar 40 has x axis 4, y axis 5 and z axis 6 and contains first layer of cleansing material 46 and second layer of cleansing material 44 juxtaposed along layer boundary 42. FIG. 6 is a cross section taken along the line 4—4 of FIG. 5. FIG. 6 also depicts x axis 4, y-axis 5 and z axis 6 of toilet bar 40 and second layer of cleansing material 44. FIG. 7 is a top planar view of another embodiment of a toilet bar 60 of the present invention. Toilet bar 60 has x axis 4, y axis 5 and z axis 6 and contains first layer of cleansing material 66 and second layer of cleansing material 64 juxtaposed along layer 62. FIG. 8 is a cross section taken along line 4—4 of FIG. 7. FIG. 8 also depicts x axis 4, y axis 5, and z axis 6 of toilet bar 60 and first cleansing layer 64 and second cleansing layer 66. FIG. 9 is a top planar view of a prior art toilet bar 50 having x axis 4, y axis 5 and z axis 6 and a first cleansing layer 54. FIG. 10, is a cross section taking along line 4—4 of FIG. 7. In FIG. 10, toilet bar 50 has x axis 6, a first cleansing material layer 54 and the second cleansing material layer 56, juxtaposed along boundary 52 which is oriented along x axis 6.

The toilet bar of the present invention may contain one or more transparent, colored, or opaque layers in any combination. Furthermore, the inventive toilet bar may contain layers with the same or different compositions. For good cohesion between adjacent layers, the composition of the layers should be compatible with each other. Usually this is achieved by minimizing the disparity in the adjacent layers formulations or by minimizing the difference in the surface free energy of the adjacent layer formulations. When a subsequent layer is poured, it may dissolve part of the previously solidified formulations at the layer's interface and therefore provide good cohesion upon solidification.

The multi-layer toilet of the present invention may contain one or more anionic detergents.

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$RO(CH_2CH_2O)_nSO_3M$ wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates being the formula:

$R^4O_2CCH_2CH(SO_3M)CO_2M;$ and amide-MEA sulfosuccinates of the formula;

$R^4CONHCH_2CH_2O_2CCH_2CH(SO_3M)CO_2M$ wherein $R^4$ ranges from $C_8$–$C_{22}$ alkyl and M is a solubilizing cation.

Sarcosinates are generally indicated by the formula:

$R^1CON(CH_3)CH_2CO_2M,$ wherein $R^1$ ranges from $C_8$–$C_{20}$ alkyl and M is a solubilizing cation.

Taurates are generally identified by formula:

$R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 70% by weight of at least one layer of the toilet bar. Preferably, this component is present from about 30% to about 60% in the layer.

The acyl isethionate may be an alkoxylated isethionate such as is described in Ilardi et al., U.S. Pat. No. 5,393,466, titled "Fatty Acid Esters of Polyalkoxylated isethionic acid; issued Feb. 28, 1995; hereby incorporated by reference. This compound has the general formula:

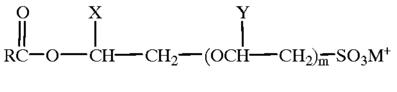

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

It should be understood that at least one layer of the bar may comprise a certain amount of soap as anionic surfactant. When used, the term "soap" is used in its popular sense, i.e., alkalimetal or alkanol ammonium salt of aliphatic alkane or alkene monocarboxylic acids. Sodium, potassium, mono-, di- and triethanol ammonium cations, or combinations thereof, are suitable for purposes of the invention. Generally, sodium soaps are used. Soaps useful herein are the well known alkali metal salts of natural or synthetic aliphatic (alkanoic or alkenoic) acids having 13 to 22 cations, preferably 12 to 18. They may be described as alkali metal carboxylates of acrylic hydrocarbons having about 12 to 22 carbons.

One or more amphoteric surfactants may be used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

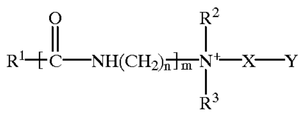

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric surfactants within the above general formula include simple betaines of formula:

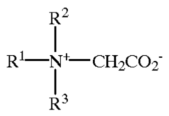

and amido betaines of formula:

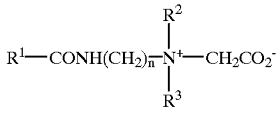

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

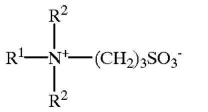

or

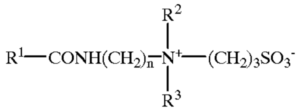

where m is 2 or 3, or variants of these in which $-(CH_2)_3SO_3^-$ is replaced by

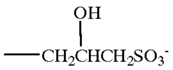

In these formulae $R^1$, $R^2$ and $R^3$ are as discussed previously.

One or more nonionic surfactants may also be used in at least one layer of the toilet bar of the present invention.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylene diamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

One or more cationic surfactants may also be used in at least one layer of the inventive multi-layer toilet bar.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol: I & II) by Schwartz, Perry & Berch, both of which are also incorporated into the subject application by reference.

The inventive multi-layer toilet bar may also contain at least one layer having 10 to 90% by wt., preferably 20 to 80% by wt. of a structurant and/or filler. Such structurant can be used to enhance the bar integrity, improve the processing properties, and enhance desired user sensory profiles.

The structurant is generally long chain, preferably straight and saturated, ($C_8$–$C_{24}$) fatty acid or ester derivative thereof; and/or branched long chain, preferably straight and saturated, ($C_8$–$C_{24}$) alcohol or ether derivatives thereof.

A preferred bar structurant is polyalkylene glycol with molecular weight between 2000 and 20,000, preferably between 3000 and 10,000. Those PEGs are commercially available, such as those marketed under the tradename of CARBOWAX SENTRY PEG8000® or PEG4000® by Union Carbide.

Other ingredients that can be used as structurant or fillers include starches, preferably water soluble starches such as maltodextrin and polyethylene wax or paraffin wax.

Structuring aids can also be selected from water soluble polymers chemically modified with a hydrophobic moiety or moieties, for example, EP-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm® (PEG modified glyceryl cocoate, palamate or tallowate) from Rewo Chemicals.

Other structuring aids which may be used include Amerchol Polymer HM 1500 (Nonoxynyl Hydroethyl Cellulose).

In addition, at least one layer of the multi-layer bar compositions of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2', 4' trichlorodiphenylether (DP300); preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Cationic polymers as conditioners which may be used include Quatrisoft LM-200 Polyquaternium-24, Merquat Plus 3330—Polyquaternium 39; and Jaguar® type conditioners.

Polyethylene glycols as conditions which may be used include:

| | |
|---|---|
| Polyox WSR-205 | PEG 14M, |
| Polyox WSR-N-60K | PEG 45M, or |
| Polyox WSR-N-750 | PEG 7M. |

Another ingredient which may be included are exfoliants such as polyoxyethylene beads, walnut shells and apricot seeds, and the like.

Compositions of the multi-layer inventive toilet bar also comprise 1% to 10% by wt., preferably 4% to 7% by wt. water.

In one embodiment of the invention, each layer's composition comprises no more than about 60% surfactant. Said composition also contains 10% to 70% by wt. structurant/filler.

Because of lower surfactant levels, such compositions would be more "drying" on the skin and such compositions would comprise 0.01 to 10% benefit agent/emollient.

The benefit agent "composition" may be a single benefit agent component or it may be a benefit agent compound added via a carrier. Further, the benefit agent composition may be a mixture of two or more compounds one or all of which may have a beneficial aspect. In addition, the benefit agent itself may act as a carrier for other components one may wish to add to the bar composition.

The benefit agent can be an "emollient oil" by which is meant a substance which softens the skin (stratum corneum) by increasing into water content and keeping it soft by retarding decrease of water content.

Preferred emollients include:

(a) silicone oils, gums and modifications thereof such as linear and cyclic polydimethylsiloxanes; amino, alkyl, alkylaryl, and aryl silicone oils;

(b) fats and oils including natural fats and oils such as jojoba, soybean, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and psuedo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) and butyl methoxy benzoylmethane (Parsol 1789);

(m) phospholipids; and (n) mixtures of any of the foregoing components, and the like.

A particularly preferred benefit agent is silicone, preferably silicones having a viscosity greater than about 10,000 centipoise. The silicone may be a gum and/or it may be a mixture of silicones. One example is polydimethylsiloxane having viscosity of about 60,000 centistokes.

The composition may also comprise decorative particulates including speckles, coloured or reflective particles, or shaped particles and the like.

Conventional art recognised cast melt processing techniques may be used to fabricate the inventive multi-layer toilet bar. For example, the melted components of the inventive bar are usually blended together at elevated temperatures. Optionally the water level may be adjusted and the blending will continue. Next an optional drying step may follow whereby the water is reduced. Finally, the molten cleaning composition is poured into molds and cooled to its hardening point. The molds may be made of any rigid material that is not subject to attack by the ingredients of the toilet bar. Mold materials may include plastic, metal, glass, ceramic, or composite materials and the like. Cooling the molten cleansing materials can be accomplished by art recognised cooling techniques including refrigeration, cryogenics, ambient air and the like. Controlled cooling using thermostatic control cooling devices may also be employed.

Conventional art recognised packaging materials may be used to package the inventive multi-layered toilet bar. The package may hold one or more separately packaged bars. The package may also have an optional transparent area to view part or all of the bar contained herein. Paper, plastic, or coated paper, or other flexible or rigid packaging materials that are compatible with the toilet bar may be used. Single layer or laminated packaging material structures may also be used. Preferably, the packaging material is moisture proof, and mold resistant. The packaging material should have good barrier properties to prevent the loss of volatile cleansing composition ingredients such as perfume. Examples, of useful barrier materials are polymer coated paper board or other appropriate materials. Hot melt adhesive or contact adhesive such as glue may be used to adhere a portion of the carton and the wrapper. An appropriate coating would be a low density polyethylene coating and the like.

EXAMPLE

Two examples of the present invention are given below by way of illustration and not by way of limitation.

In both examples, a two-layer cleansing bar according to the present invention, having a clear and a colored cleansing layer oriented along a plane perpendicular to the plane formed by the x and y-axis of the bar was prepared having the formula listed below.

| INGREDIENT | TRANSPARENT | COLORED |
|---|---|---|
| 80/20 Tallow/Coco Soap Base | 40 | 40 |
| Water | 6 | 6 |
| Sucrose (70% Solution In Water) | 24 | 24 |
| Triethanolamine | 5 | 5 |
| Propyleneglycol | 15 | 15 |
| Ethyl Alcohol | 10 | 10 |
| Colour (D&C Green) | 0 | 0.1 |
| TOTAL | 100% | 100.1% |

The ingredients were blended together at a temperature of approximately 90° C. in separate mixing vessels, with occasional stirring. All concentrations are expressed as a weight/weight percentage. A unitary elastomeric polymer mold having a substantially ovoid shape cavity size at 92 mm along its x axis, 64 mm along its y axis, and 35 mm along its z axis was used. A ⅛ inch thick, single sinusoidal shaped plastic divider, having an amplitude of 8 mm, was slidably positioned in the cavity along the bar's axis and perpendicular to the plane formed by the x and y-axis of the bar. In the first example, the transparent molten mixture at a temperature of 90° C. was poured into one side of the mold and allowed to air cool for one hour until it was hardened. The divider was then removed and the colored molten mixture at a temperature of 90° C. was then poured into the mold cavity and also allowed to air cool for one hour until it was hardened. The bar was then easily ejected from the mold.

In the second example, the transparent the colored molten mixture at 90° C. were poured simultaneously into the divided cavities and the removable divider was removed before the melt had cooled below 85° C.

The bars were tested under shower conditions at 100% RH with approximately 115 F water. Nine washes and two drops from a height of 42 inches were used. The toilet did not fracture or break during the testing.

Toilet bars produced by the sequential pouring and cooling technique have a sharp boundary between the two phases. Production time may however be reduced (e.g. cooling time may be reduced by ⅓) when the toilet bars are produced by the simultaneous or near simultaneous pouring of the molten components into the mold. The divider is then removed before any of the components cool to the point that neither component flows, preferably at a temperature equal to or greater than 85° C. The divider may be removed at temperatures below 85° C. if lower melting components are used which still flow at such lower temperatures.

Toilet bars produced by the simultaneous pour method are seen to have a distinct separation which follows the divider shape along the face of the bar that touches the inside or bottom face of the mold, i.e. the end opposite the open end. On the other hand, the side of the bar adjacent to the open end of the mold usually takes on a more linear and less distinct separation of the phases, notwithstanding the shape of the removable divider.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

What is claimed is:

1. A multi-layered toilet bar comprising:

a plurality of layers of cleansing material, said layers having at least one common interface along said bar's major axis; and at least two of said layers having been melt cast in a unitary mold having a cavity, wherein said melt casting is a continuous process whereby said casting is not removed from said mold prior to completion of casting said toilet bar.

2. The multi-layered toilet bar of claim 1, wherein said unitary mold has one removable, formed divider, and said toilet bar has two layers of cleansing material.

3. The multi-layered toilet bar of claim 1, wherein said at least one removable, formed divider in a first position divides said cavity into at least two cavities, said at least one divider being individually and slidably removed from said cavity in a second position.

4. The multi-layered toilet bar of claim 1, wherein said at least one removable, formed divider in a first position divides said cavity into at least two cavities, said at least one divider being individually and pivotally removed from said cavity in a second position.

5. The multi-layered toilet bar of claim 1, wherein said at least one removable formed divider is composed of a material selected from the group consisting of a solid water soluble or dispersible material, metal, plastic, glass, ceramic, or a composite material.

6. The multi-layered toilet bar of claim 1, wherein at least one of said formed dividers has a curvilinear shape.

7. The multi-layered toilet bar of claim 1 wherein at least one layer is composed of a cleansing material which lathers and at least one layer is composed of a cleansing material which moisturizes.

8. The multi-layered toilet bar of claim 1 wherein at least one removable formed divider is a solid water soluble or dispersible material which becomes a part of said toilet bar.

9. A melt casting process for making a multi-layered toilet bar, comprising the steps of:

positioning at least one removable, formed divider along a plane perpendicular to the plane formed by the x and y-axis of said bar in a unitary mold having a cavity, to form at least two cavities;

pouring a first molten cleansing material into a first cavity defined by said mold and said at least one removable divider;

cooling said first molten cleansing material until it is hardened;

removing said at least one divider from the mold;

pouring a second molten cleansing material into a second mold cavity defined by said hardened first cleansing material and said mold;

cooling said second molten cleansing material until it is hardened; and ejecting a hardened multi-layered toilet bar casting from said mold.

10. The process of claim 9, wherein said melt casting is a continuous process whereby said casting is not removed from said mold prior to the completion of the casting.

11. The process of claim 9 wherein one removable divider in a first position divides said divisible cavity into a first cavity and a second cavity, said divider being slidably removed from said cavity in a second position.

12. The process of claim 9, wherein one removable divider in a first position divides said cavity into a first cavity and a second cavity, said divider being pivotally removed from said cavity in a second position.

13. The process of claim 9, wherein each of said formed dividers is composed of a material selected from the group consisting of a water soluble or dispersible material, metal, plastic, glass, ceramic, or a composite material.

14. The process of claim 9, wherein each of said formed dividers has a curvilinear shape.

15. The process of claim 9, wherein at least one cleansing material lathers and said at least one second cleansing material moisturises.

16. The process of claim 9, wherein each of said molten cleansing materials are cooled by a method selected from the group consisting of refrigeration, cryogenics, or exposure to ambient air.

17. A melt casting process for making a multi-layered toilet bar, comprising the steps of:

positioning at least one formed divider along a plane perpendicular to the plane formed by the x and y-axis of said bar in a unitary mold having a cavity to form at least two cavities;

pouring a first molten cleansing material into a first cavity defined by said mold and said at least one formed divider;

pouring a second molten cleansing material into a second cavity defined by said mold and said at least one formed divider;

cooling said first and second cleansing material until they are hardened;

ejecting a hardened, multi-layered toilet bar casting incorporating said at least one formed divider from said mold; and said at least one formed divider contains a water soluble or dispersible composition.

18. The process of claim 17 wherein said at least one formed divider contains a cleansing composition with a higher melting point then its adjacent cleansing composition places.

19. A melt casting process for making a multi-layered toilet bar, comprising the steps of:

positioning at least one removable, formed divider along a plane perpendicular to the plane formed by the x and y-axis of said bar in a unitary mold having a cavity, to form at least two cavities;

pouring at least two molten cleansing materials into said at least two cavities at a first temperature;

cooling said molten cleansing materials to a second temperature wherein at least one of said materials remain flowable;

removing said at least one divider from the mold at said second temperature;

cooling said molten materials until they are hardened; and ejecting a hardened multi-layered toilet bar casting from said mold.

20. The process of claim 19 wherein said second temperature is equal to or greater than 85° C.

* * * * *